United States Patent
Bettuchi et al.

[11] Patent Number: 5,935,132
[45] Date of Patent: Aug. 10, 1999

[54] SURGICAL GUIDE AND CUTTING SYSTEM

[75] Inventors: Michael J. Bettuchi, Randolph; Erik S. Larson, Norwood; Richard C. Techiera, Avon, all of Mass.

[73] Assignee: Johnson & Johnson Professional, Inc., Raynham, Mass.

[21] Appl. No.: 08/988,563

[22] Filed: Dec. 10, 1997

[51] Int. Cl.$^6$ ..................................................... A61F 5/00
[52] U.S. Cl. ............................. 606/87; 606/80; 606/86; 606/88; 606/89
[58] Field of Search ................................. 606/86, 87, 88, 606/89, 80

[56] References Cited

U.S. PATENT DOCUMENTS

| | | | |
|---|---|---|---|
| 4,474,177 | 10/1984 | Whiteside | 128/303 |
| 4,721,104 | 1/1988 | Kaufman et al. | 128/92 |
| 4,722,330 | 2/1988 | Russell et al. | 128/92 |
| 5,098,436 | 3/1992 | Ferrante et al. | 606/88 |
| 5,176,684 | 1/1993 | Ferrante et al. | 606/86 |
| 5,258,032 | 11/1993 | Bertin | 623/20 |
| 5,380,333 | 1/1995 | Meloul et al. | 606/80 |
| 5,415,662 | 5/1995 | Ferrante et al. | 606/86 |
| 5,474,559 | 12/1995 | Bertin | 606/89 |
| 5,554,158 | 9/1996 | Vinciguerra et al. | 606/80 |
| 5,569,259 | 10/1996 | Ferrante et al. | 606/87 |
| 5,676,668 | 10/1997 | McCue et al. | 606/87 |
| 5,690,637 | 11/1997 | Wen et al. | 606/88 |
| 5,720,752 | 2/1998 | Elliott et al. | 606/88 |
| 5,735,856 | 4/1998 | McCue et al. | 66/87 |

OTHER PUBLICATIONS

Johnson & Johnson Orthopaedics Product Brochure entitled *P.F.C Sigma Knee System*, pp. 13–14, 1997.
Johnson & Johnson Orthopaedics Product Brochure entitled *P.F.C. ®Sigma, Primary Cruciate–retaining & Cruciate–Substituting Procedures*, Surgical Technique for Use with P.F.C.®, Sigma Knee System, pp. 63–65, Feb. 1996.
Johnson & Johnson Orthopaedics Product Brochure entitled *P.F.C. ®Sigma Knee System*, pp. 13–14, 1997.

*Primary Examiner*—Michael Buiz
*Assistant Examiner*—(Jackie) Tan-Uyen T. Ho
*Attorney, Agent, or Firm*—Nutter, McClennen & Fish, LLP

[57] ABSTRACT

A guide and cutting system is provided that is effective to accurately and efficiently resect a bone, such as the femur, to accept joint prosthesis components. In particular, the guide and cutting system of the invention is useful to resect the distal end of the femur to form an intercondylar notch therein that will accept a posterior stabilized femoral component in the prosthesis. The system includes a guide component that with a square bushing is attachable to bone or to a separate guide assembly. A cutting device that includes a rotatable cutting device disposed inside a non-rotatable housing is insertable within the guide bushing to effect bone resection.

17 Claims, 10 Drawing Sheets

SURGICAL GUIDE AND CUTTING SYSTEM

CROSS REFERENCE TO RELATED APPLICATIONS

Not applicable.

STATEMENT REGARDING FEDERALLY SPONSORED RESEARCH

Not applicable.

FIELD OF THE INVENTION

The invention relates to devices and a system for use in orthopedic surgery. More particularly, the invention relates to bone-resecting devices and guides useful in joint replacement surgery.

BACKGROUND OF THE INVENTION

Replacement of joints, such as knees and hips, with artificial joints or joint prostheses has become quite common. During the course of joint replacement surgery it is necessary to prepare a bone, by shaping and resection techniques, to receive a prosthetic element. Several specialized guide and cutting devices are utilized to prepare the bone by accurate shaping and resection procedures.

The success of joint replacement surgery depends to a large extent on the proper placement of a prosthetic component upon a patient's bone. It is therefore essential that the bone receiving the prosthesis be properly prepared and resected. Accordingly, cutting and guide devices which assist surgeons in making precise cuts and resections to bone can contribute greatly to the success of joint replacement surgery.

Some patients undergoing knee arthroplasty require a posterior stabilized knee prosthesis femoral component which includes an intercondylar box. Implantation of such a prosthesis requires the resection of an intercondylar notch within the femur. The accuracy of the resection of the intercondylar notch is critical to the proper alignment of the prosthesis. A variety of guide and cutting devices are available to assist surgeons in properly resecting the patient's bone.

U.S. Pat. No. 5,098,436 discloses modular surgical instrumentation for use in shaping the femur during knee replacement surgery. An advantage attributed to this instrument is that a patella groove may be formed in the femur utilizing a cutting guide which need not be removed in order to form a recess for an intercondylar stabilizing housing using a second cutting guide.

U.S. Pat. No. 4,721,104 discloses an apparatus for accurately placing and forming a recess in a distal portion of the femur to accommodate an intercondylar stabilizing housing of a posterior-stabilized knee implant prosthesis. Other such guides and cutting devices are disclosed by U.S. Pat. Nos. 5,176,684; 5,258,032; 5,415,662; 5,474,559; 5,554,158; and 5,569,259.

Instruments such as those described in the references noted above have helped to improve the accuracy of bone resection, particularly preparation of the distal portion of a femur for the introduction of a prosthesis, such as a posterior stabilized prosthesis. However, there remains a need for devices that are able to provide more accurate and effective bone resection. In addition, there is a need for modular devices that can effectively be used to resect different intercondylar notch widths and depths to accept different sized prostheses while using a minimum number of parts.

SUMMARY OF THE INVENTION

The present invention provides a surgical guide and cutting system that is particularly useful for the accurate preparation of a bone to receive a prosthesis component. The system comprises a first guide assembly that is mountable in proximity to a bone to be prepared. This guide assembly has at least one guide bushing that is mountable thereon in alignment with a surface of a bone to be prepared. The location of the bushing may be adjusted to guide a cutting device to a desired location. The system may also include a variety of different sized guide bushings that may be removably and replaceably mounted upon the first guide assembly.

The system also includes at least one cutting element which is insertable within a suitably sized guide bushing. The cutting element includes a rotating bone cutting element that is disposed within a housing having a shape that is complementary to the guide bushing, enabling the housing to fit within the guide bushing. The rotatable bone cutting element has a distal end with a bone cutting surface that is able to protrude from the housing, and a proximal end that protrudes from a proximal end of the housing. The portion of the rotatable bone cutting element that protrudes from the proximal end of the housing can be attached to a power reamer or another suitable drill device to effect rotation of the cutting element.

In one embodiment the system also includes a second guide assembly that is mounted directly upon the bone to be prepared. In this embodiment, the first guide assembly comprises a fixation block mountable upon the second guide assembly and a face plate that is adjustably mounted on the fixation block. The face plate preferably has a bone-facing opening formed therein. A locking element is provided to secure the face plate in a desired position relative to the fixation block. Further, the system includes a suitable mechanism for affixing one of the guide bushings to the face plate such that the guide bushing communicates with the bone-facing opening of the face plate.

BRIEF DESCRIPTION OF THE DRAWINGS

The invention will be more fully understood from the following detailed description taken in conjunction with the accompanying drawings and claims.

DETAILED DESCRIPTION OF THE INVENTION

The present invention provides a guide and cutting system that is useful to accurately resect a portion of a bone to accept a prosthesis component, such as a posterior stabilized prosthesis component. In particular, the system of the invention is useful to resect a distal end of the femur, by forming an intercondylar notch, to prepare this bone to accept a posterior stabilized femoral component of a knee prosthesis.

Figure 3:
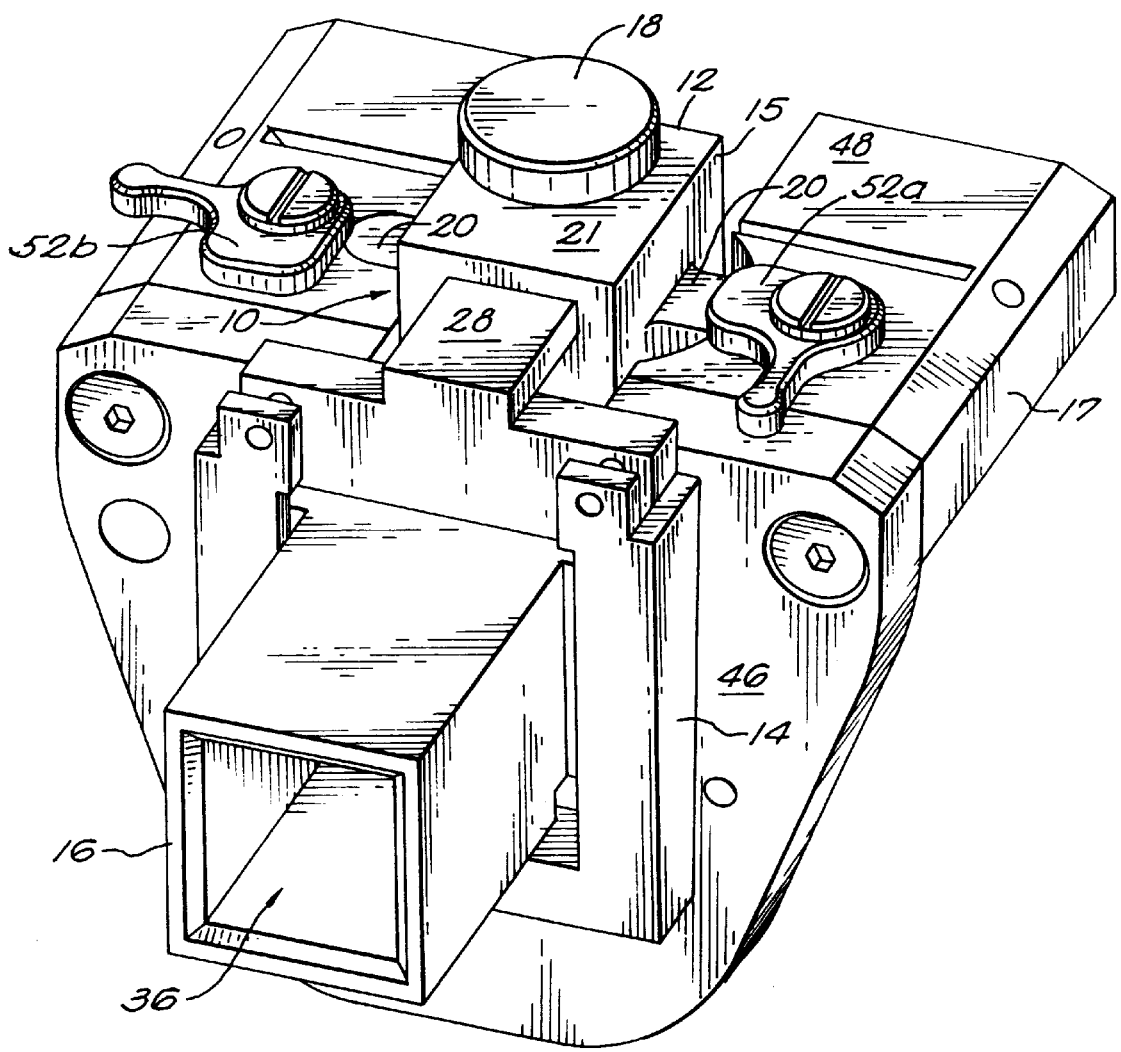
FIG. 3 is a perspective view of a guide assembly according to the present invention which is mounted upon a femoral notch guide.

The system of the invention includes a first guide assembly 10 having a fixation block 12, which is matable with a face plate 14. The face plate 14 is, in turn, matable with a guide bushing 16. As shown in FIG. 3, the first guide assembly may be mounted upon a second guide assembly, such as a femoral notch guide 17. The femoral notch guide, as shown in FIGS. 4–9, is mountable upon a distal end of a femur 19 to effect the formation of an intercondylar notch in the femur.

Figure 1:
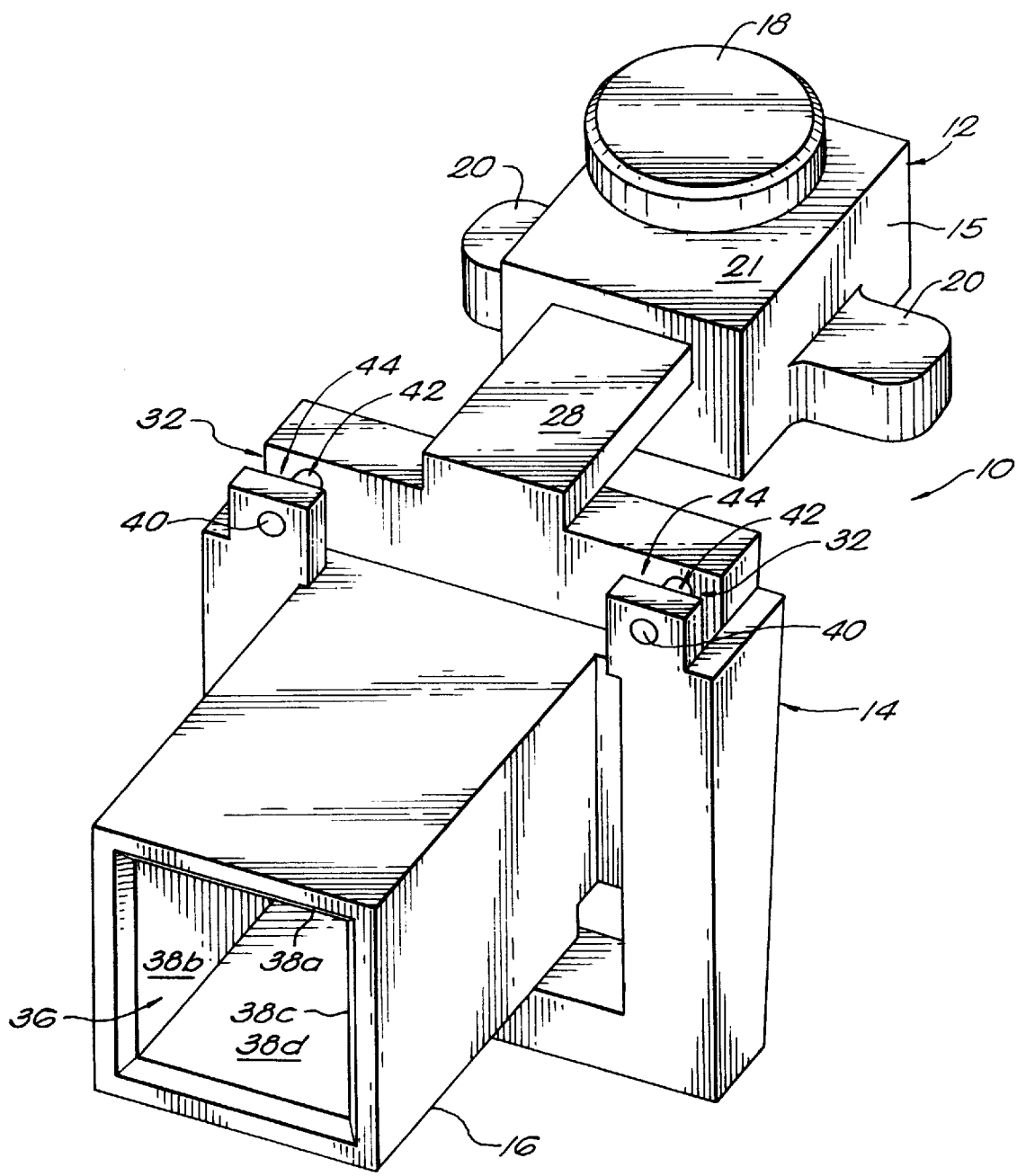
FIG. 1 is perspective view of a guide assembly useful with the system of the present invention.
Figure 2:
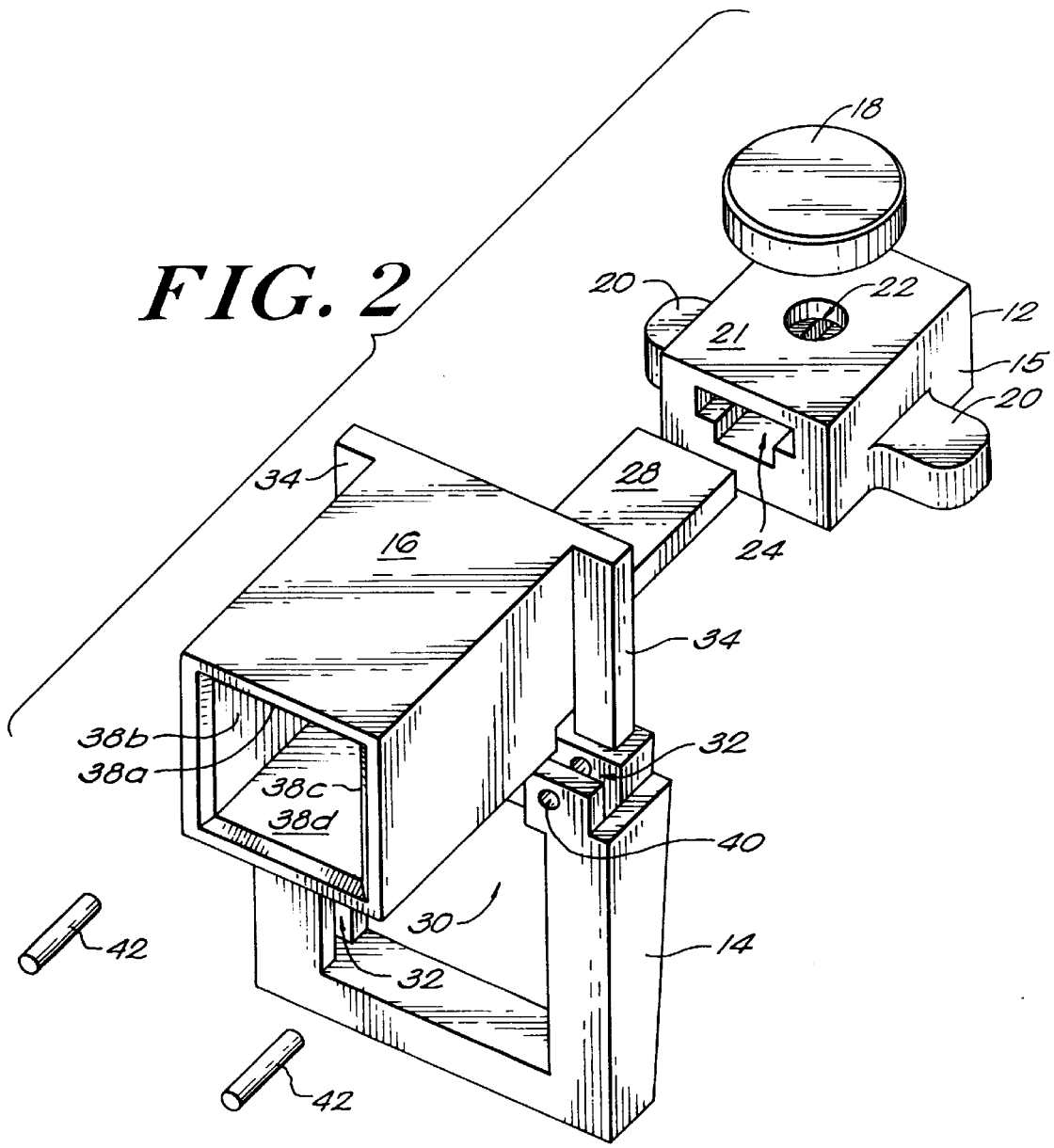
FIG. 2 is an exploded view of the guide assembly of FIG. 1.

Referring to FIGS. 1–3, the fixation block 12 of the first guide assembly 10 includes a substantially square or rectangular block member 15 which has engagement flanges 20 extending from opposite sides of the block member. The fixation block 12 also includes an axially oriented slot 24 and an aperture 22 that is formed on the top surface 21 of block.

FIGS. 1–3 and 10 and 11 illustrate the face plate 14, which includes a substantially square member having opposed side walls 26a, 26b and top and bottom walls 26c, 26d. A mounting flange 28 extends posteriorly from the top wall 26c and is dimensioned to fit within the slot 24 of the fixation block 12. Upon mating the mounting flange 28 within slot 24 to secure the face plate to the fixation block, thumb screw 18, which contacts the mounting flange through aperture 22, can be used to secure the face plate to the fixation block in a desired position.

The side, top and bottom walls 26a–d of the fixation block define a bone-facing opening 30 which may be substantially square or rectangular. Further, a pair of opposed channel tracks 32 are formed in side walls 26a and b. In one embodiment the opposed channel tracks are vertically oriented and extend over the height of the side walls. The thickness (T) of the channel tracks 32 should be sufficient to accept the opposed flanges 34 of the guide bushing 16. Typically, the thickness of the channel tracks 32 is in the range of 0.1 inch to 0.15 inch, and typically about 0.125 inch.

The bone-facing opening 30 of the face plate 14, when operatively assembled to the femur, communicates with the anterior surface 35 of the femur 19. In the illustrated embodiment, bone-facing opening 30 is square. However, it is understood that this opening may assume a variety of alternative shapes. The dimensions of the bone-facing opening 30 can vary depending upon a variety of factors including the type of surgery involved and the size and shape of the prosthesis to be implanted. Generally, however, a square bone-facing opening will be such that each wall defining the opening will have a length in the range of about 1.140 inches to 1.150 inches.

The guide bushing, as shown in FIGS. 1–3, 12 and 13 is a box-like member that includes at a posterior portion opposed guide flanges 34. An anterior portion of the guide bushing 16 includes a square opening 36 which traverses the box-like member from the anterior to the posterior end. This opening is defined by top, side and bottom walls 38a–d. These walls define a square bushing that extends over a length L of about 1.485 inches to 1.515 inches.

The guide flanges 34 preferably have a thickness (T) that enables them to be mated within the opposed channel tracks 32 without undue interference, but with a fit that is sufficient to prevent undue movement of the guide bushing in the anterior-posterior direction. The width (W) and height (H) of the guide flanges 34 of the guide bushing 16 should be of dimensions such that there is sufficient freedom of movement within the face plate in the vertical and horizontal (i.e., medial-lateral) directions to enable the square opening 36 of the guide bushing to cover the entire area of the bone-facing opening 30 of the face plate. In an exemplary embodiment, the guide bushing is free to travel within the face plate in a horizontal (i.e., medial-lateral) direction by a distance of about 0.05–0.3 inch on either side of a central position, and typically about 0.1 inch. The guide bushing is free to move vertically (i.e., proximally and distally) within the face plate by a distance of about 0.1 to 0.4 inch on either side of a central position.

The guide bushing 16 can be secured within the face plate by a variety of mechanisms that will ensure its ability to remain free to move horizontally and vertically within the face plate. In an illustrated embodiment, the face plate 14 includes apertures 40 which house dowel pins 42. In one embodiment, the bushing may be pre-assembled within the face plate. Once the bushing is mated with the face plate, the dowels 42 are inserted through apertures 40 to prevent removal of the guide bushing 16 from opening 44 in the face plate 14. Accordingly, while the guide bushing is secured within the face plate the relative dimensions of the guide flanges 34 and the channel tracks 32 permit horizontal and vertical motion of the guide bushing 16 relative to the face plate 14. Although the opening 44 is shown to be at a top portion of the face plate, one of ordinary skill in the art will readily appreciate that this opening may be present on the face plate in alternative positions.

Figure 4:
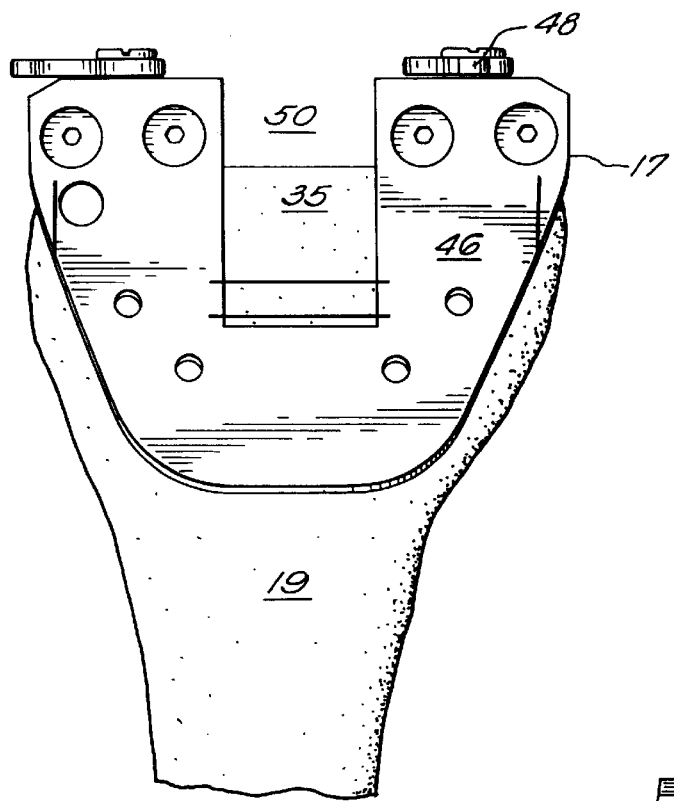
FIG. 4 is a top view of a femoral notch guide mounted upon a femur.
Figure 5:
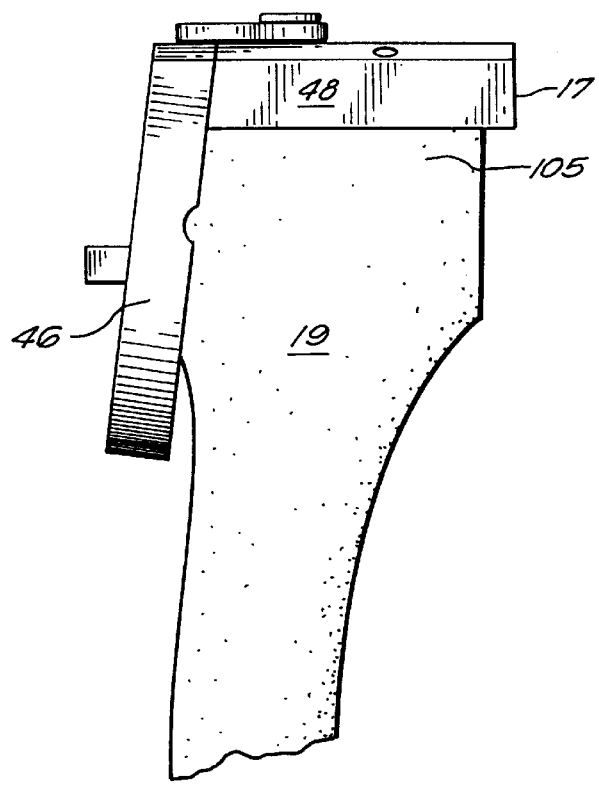
FIG. 5 is a side view of the femoral notch guide of FIG. 4.

The first guide assembly 10 of the invention may be mounted directly to bone or to other guide instruments which themselves are mounted directly to bone. In an embodiment illustrated in FIG. 3, the first guide assembly 10 is mounted to a femoral notch guide 17. A femoral notch guide, which is a guiding instrument known to those having ordinary skill in the art, may be affixed to the distal end 105 of a femur 19 as shown in FIGS. 4 and 5. The femoral notch guide includes an anterior surface 46 which is joined to a distal surface 48 at a fixed angle (e.g., about 95°). A central notch or opening 50 is formed in the anterior surface 46.

The first guide assembly 10 may be mounted to the femoral notch guide in the manner illustrated in FIG. 3. That is, the engagement flanges 20 of the fixation block 12, which are formed on medial and lateral sides of the fixation block, may be seated within a recess (not shown) on the distal surface 48 of the femoral notch guide 17. Locking mechanisms, such as locking levers 52a and 52b, may be selectively activated to positively secure the engagement flanges 20 to the femoral notch guide. As illustrated in FIG. 3, locking lever 52a is in a closed position while locking lever 52b is in an open position.

When properly positioned on the femoral notch guide, the face plate 14 abuts the anterior surface 46 of the femoral notch guide and the bone-facing opening 30 is aligned with the notch 50 of the bone-facing opening. Moreover, the guide bushing 16 protrudes anteriorly from the face plate such that the square opening is aligned with the bone-facing opening 30 and the notch 50.

Figure 6:
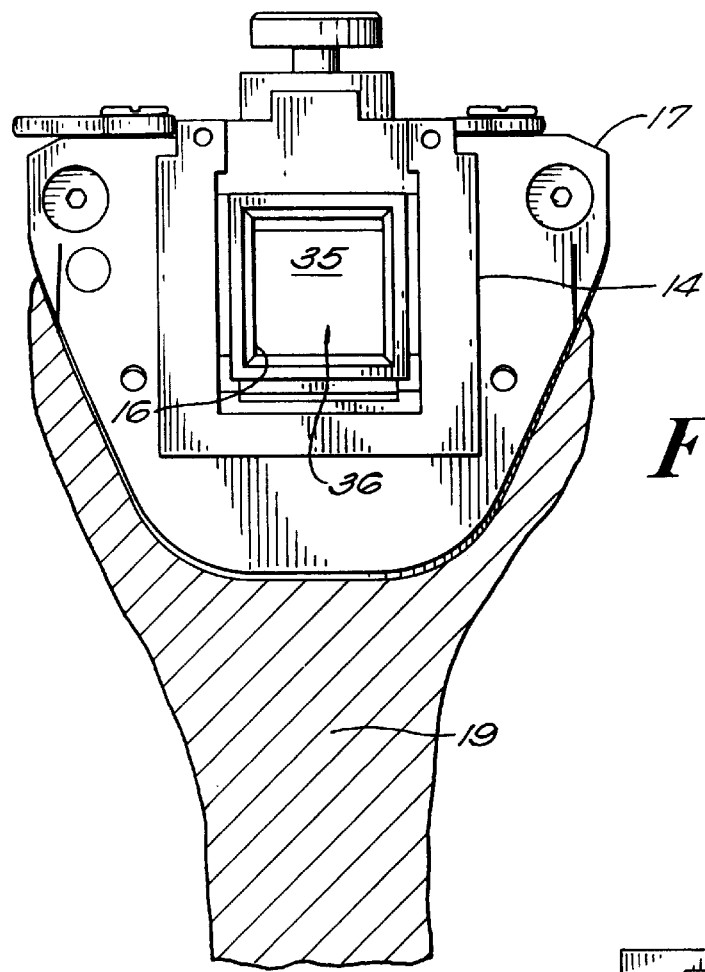
FIG. 6 is a top view of a guide assembly useful with the system of the present invention mounted upon the femoral notch guide of FIG. 4.
Figure 7:
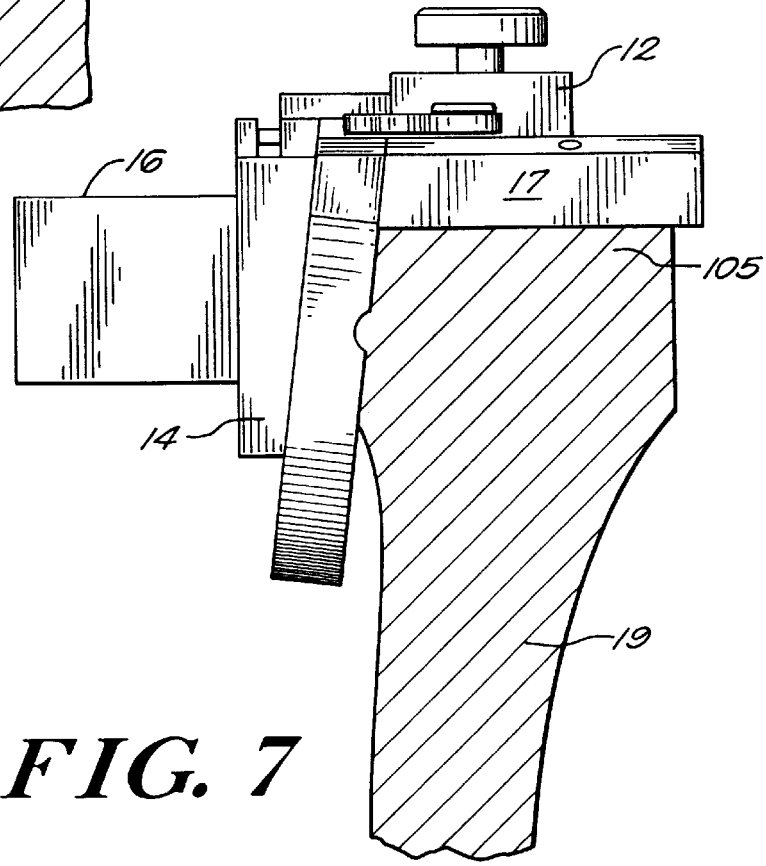
FIG. 7 is a side view of the system shown in FIG. 6.
Figure 8:
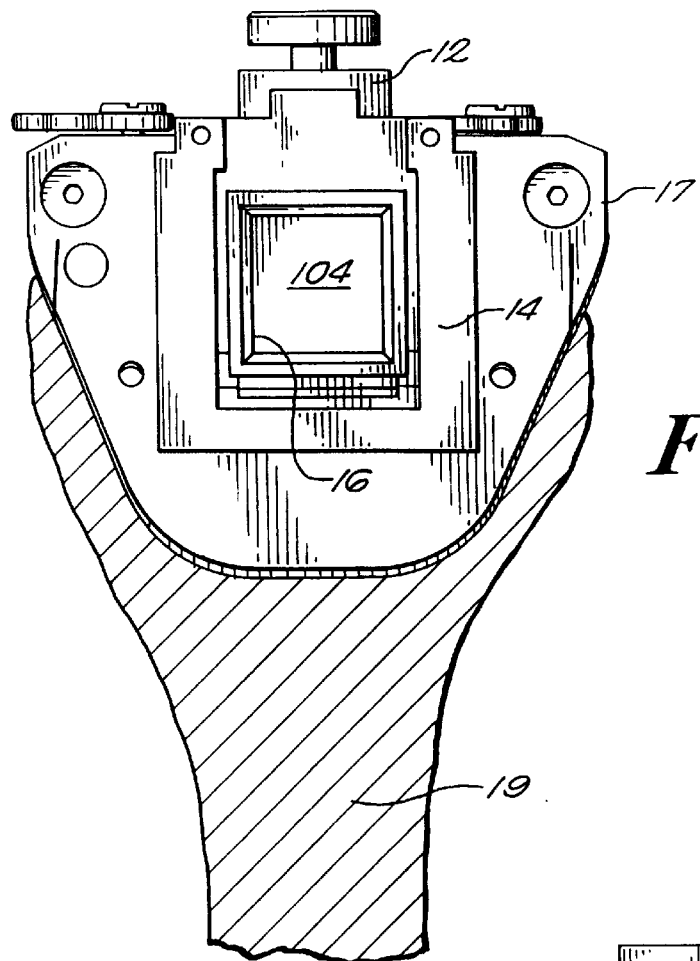
FIG. 8 is a top view of the system of FIG. 6 following resection of the femur.
Figure 9:
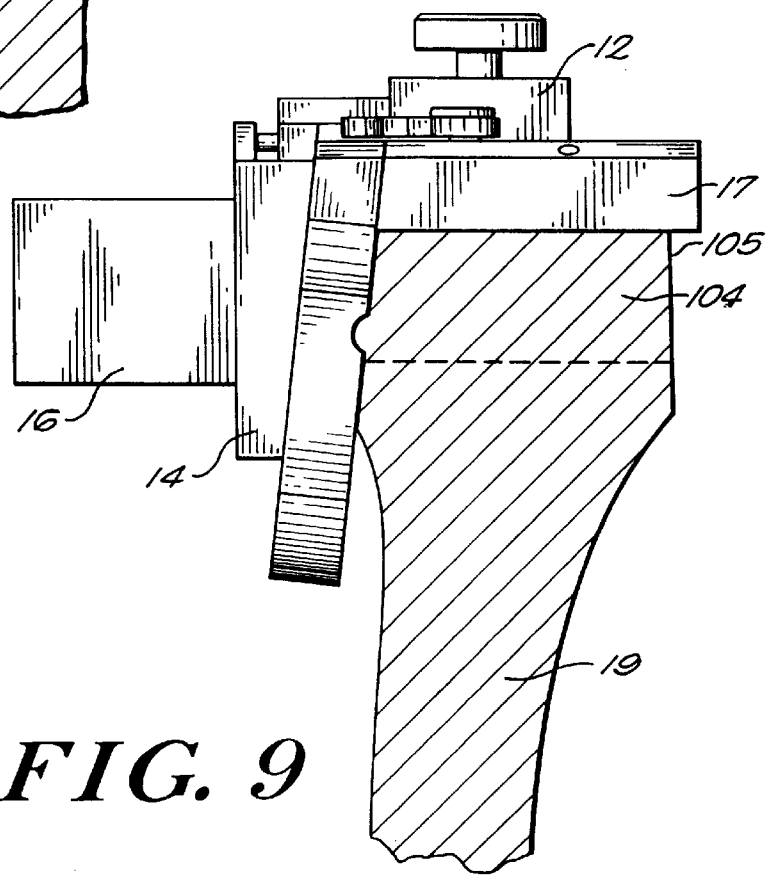
FIG. 9 is a side view of the system of FIG. 8.
Figure 10:
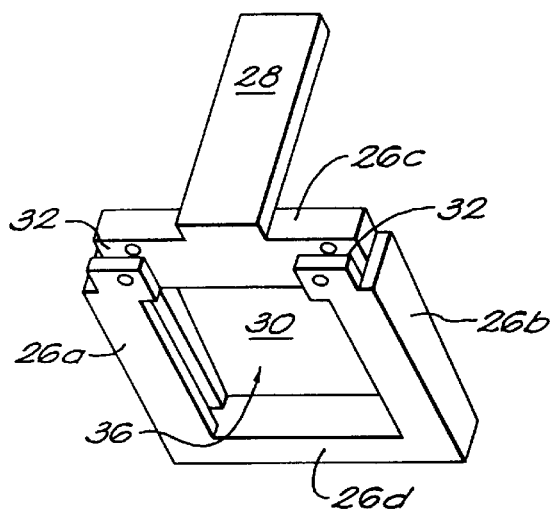
FIG. 10 is a perspective view of a face plate useful with the guide assembly of the invention.
Figure 11:
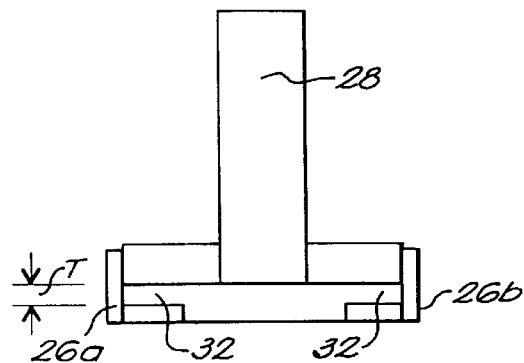
FIG. 11 is a top view of the face plate of FIG. 10.
Figure 12:
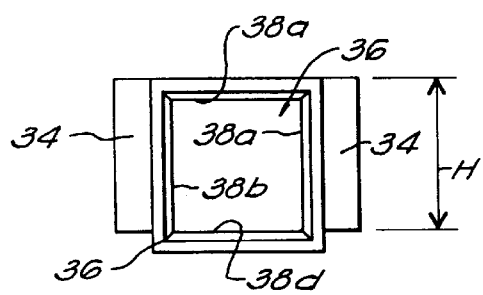
FIG. 12 is a front view of a guide bushing useful with the system of the present invention.
Figure 13:
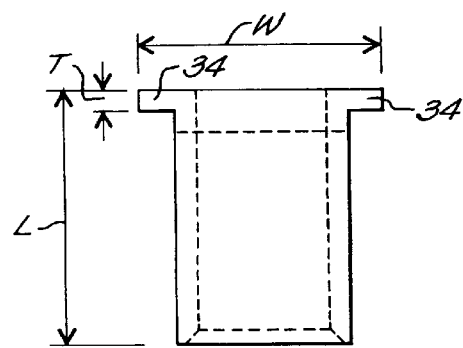
FIG. 13 is a top view of the guide bushing of FIG. 12.

FIG. 6 and 7 illustrate the femoral notch guide 17 and the first guide assembly 10 mounted upon a femur 19. As illustrated, when properly mounted upon the femur, these components enable the square opening 36 to be aligned with the bone-facing opening 30 and the notch 50 to expose a distal portion 35 of the femur.

Figure 14:
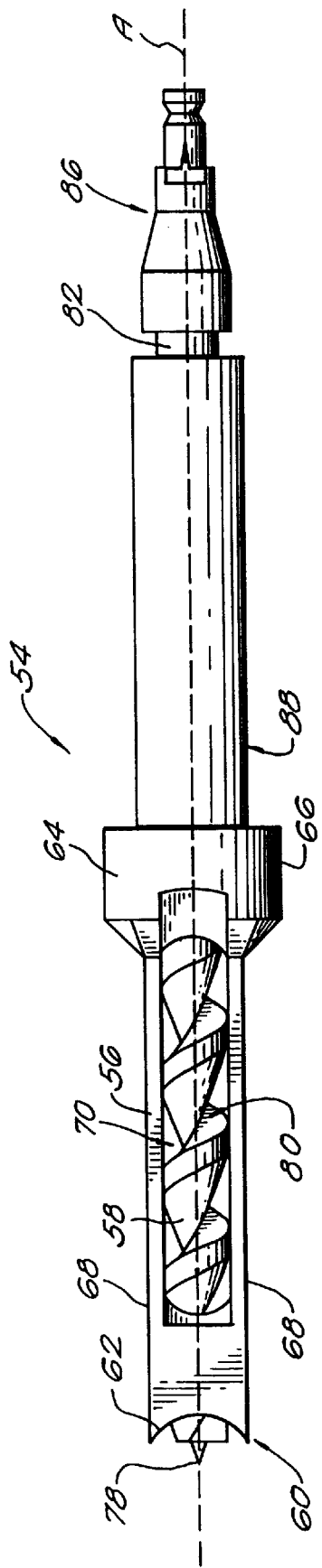
FIG. 14 is a side view of a cutting element useful with the system of the invention
Figure 15:
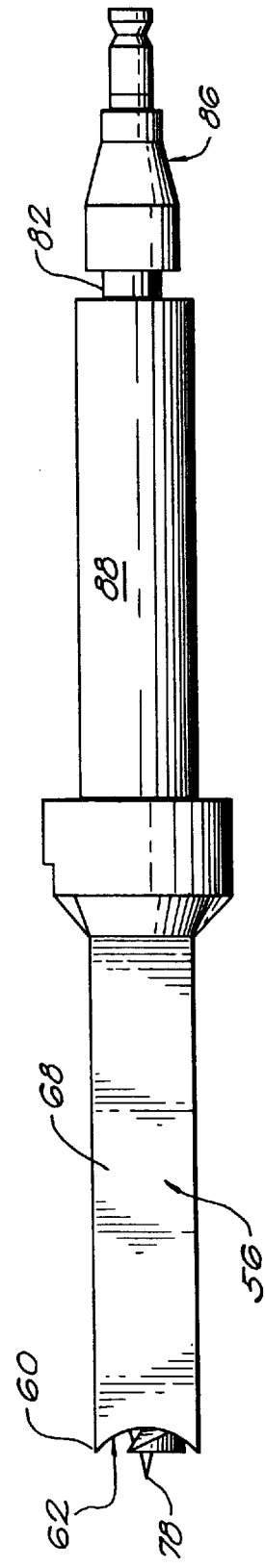
FIG. 15 is a side view of the cutting element of FIG. 14, rotated 90°.
Figure 16:
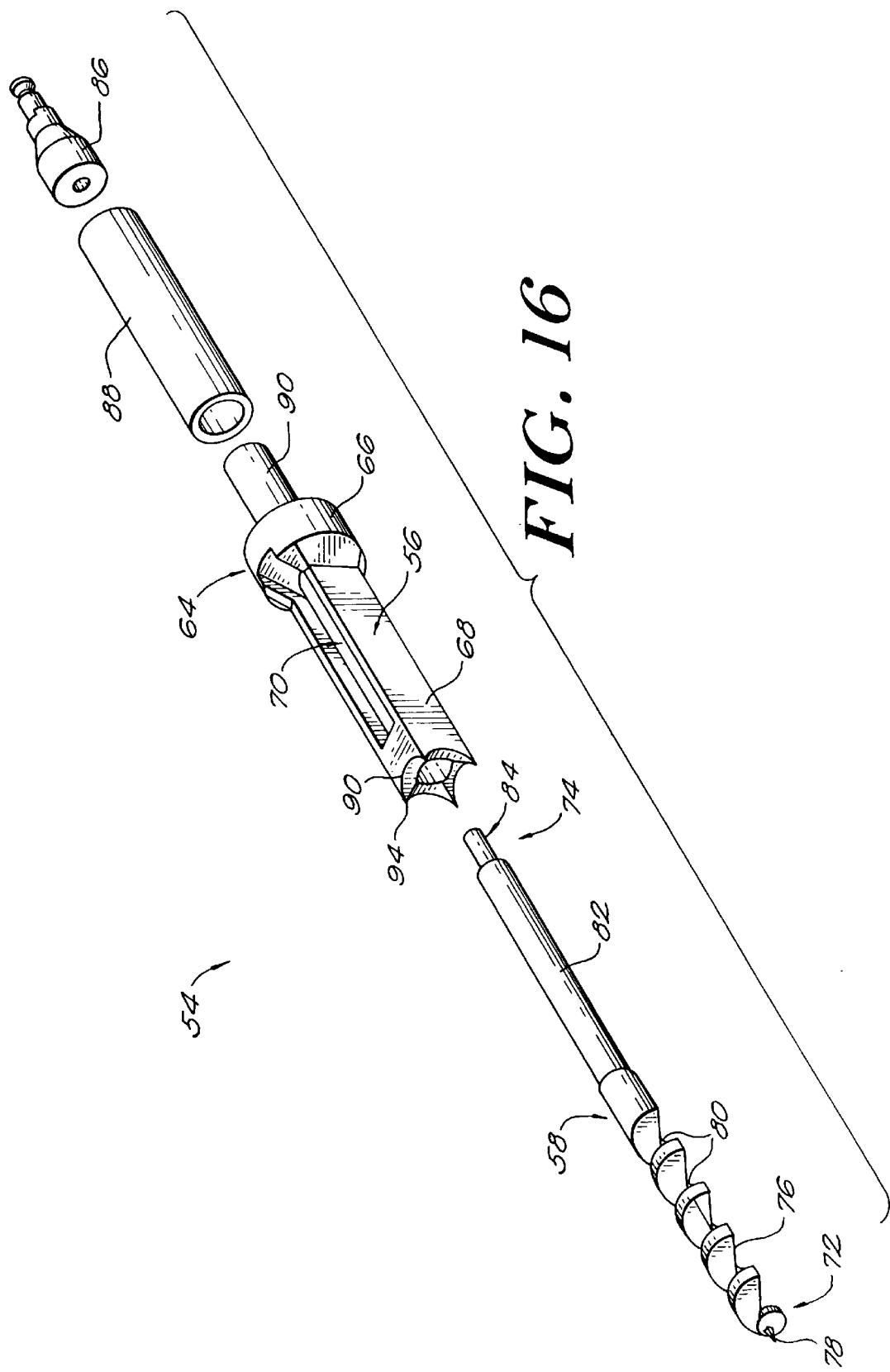
FIG. 16 is an exploded view of a cutting element useful with the present invention.
Figure 17A:
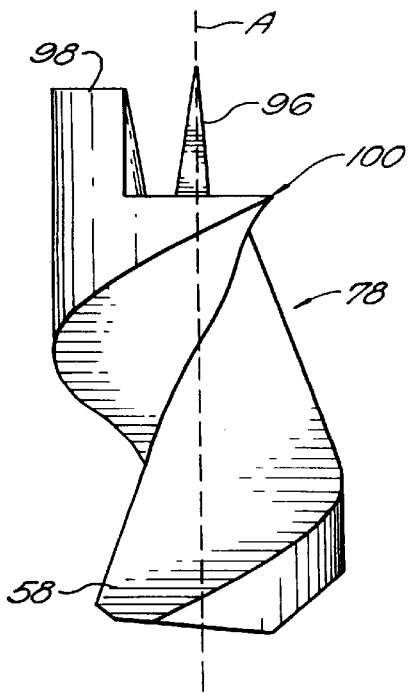
FIG. 17A is a side view of an exemplary distal end of a rotatable cutting member useful with the present invention.
Figure 17B:
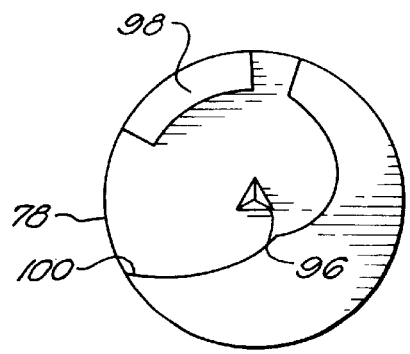
FIG. 17B is a top view of the distal end shown in FIG. 17A.
Figure 17C:
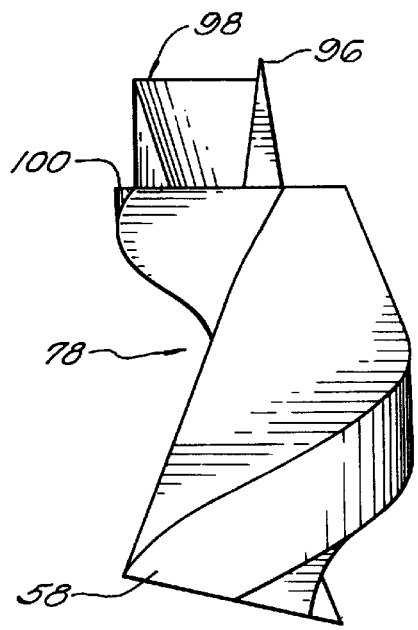
FIG. 17C is a side view, rotated 90°, of the distal end shown in FIG. 17A.

The system of the invention also includes a cutting element 54 having a rotatable cutting member 58 disposed within a non-rotatable housing 56 as illustrated in FIGS. 14–16. The housing 56 is a hollow member, which may have a square profile. Housing 56 includes a distal end 60 with a central opening therein defined by bone engaging surface features 62. The housing further includes a proximal end 64 that has a collar 66 with a mating neck 90 extending therefrom. As shown in FIGS. 14–16, the housing is an elongate, hollow member having side walls 68. At least one side wall may include an opening 70 that enables bone fragments to be ejected from within the housing.

The rotatable cutting member 58 includes distal and proximal portions 72, 74. The distal portion 72 includes a drill element 76 with a sharp, distal tip 78 and spiral grooves 80 that channel bone debris and shavings proximally, away from the tip 78.

The proximal portion 74 of the cutting/chiseling element 58 includes a shaft 82 with a proximal tip 84. In one embodiment the proximal tip 84 may be threaded so as to be connected to a quick connect structure 86 such as a Hudson end, which, in turn, may be connected to a device such as a power reamer (not shown) that also has a quick connect structure such as a Hudson end.

Referring to FIGS. 14–16, the proximal portion 74 of the rotatable cutting member 58 protrudes proximally from the collar 66 of the housing 56. In one embodiment, a sleeve 88, which may be a nonrotatable element, is disposed over the shaft 82 to mate with a mating neck 90 that protrudes proximally from the housing 56.

The cutting element 54 of the invention operates in a manner similar to that of a mortising chisel in that it acts to drill and chisel bone simultaneously. In use, the power reamer, or other device that effects rotation of the cutting/chiseling element 58, causes the cutting member 58 to rotate and to advance into the bone to be cut. As the reamer advances the rotatable cutting element 58, the sleeve 88 advances linearly, thus causing the housing to likewise advance into bone. Consequently, the bone engaging surface features 62 of the housing impact upon bone in a chisel-like manner, while the rotatable cutting member 58 advances linearly to bore through bone.

One of ordinary skill in the art will readily appreciate that the bone engaging surface features 62 of the housing 56 and the distal tip 78 of the rotatable cutting member 58 may assume different geometries. The cutting element 58 should be effective to drill a square or a rectangular opening in the bone, in a manner somewhat similar to a mortising chisel. To effect the chiseling function, the distal end 60 of the housing has four sides, each with a sharpened proximally scalloped edge 92. Each side joins an adjacent side in a sharp distally oriented tip 94.

The distal tip 78 of the rotating cutting member 58 may have virtually any shape that is suitable for penetrating bone. In one embodiment, distal tip 78, illustrated in FIGS. 14–17C, has a complex shape that consists of three entities. A pointed pyramid-shaped protrusion 96 is located on the axis of revolution (A) of the member 58. The tip 78 also includes a sharpened fin 98 which sweeps in a circle when the member 58 is rotated. The tip 78 further includes a sharp, chisel-like surface 100 that chips away material in the circular path as the member 58 rotates. The pyramid-shaped protrusion can act as a lead or centralizer to prevent the member 58 from moving away from its desired location. The fin 98 describes a circle which is the perimeter of the material which will be removed by the cutting element. The chisel edge 100 then bites into and removes the desired material.

The system of the invention can be used in the following manner. In one embodiment a femoral notch guide 17 can be attached to the distal end of the femur 19 as shown in FIGS. 4 and 5. Thereafter, the guide assembly 10 can be joined to the femoral notch guide 17 as shown in FIGS. 3, 6 and 7. As so joined, a distal portion 35 of the femur is accessible through the square opening 36 of the guide bushing 16. To form an intercondylar notch 104 in the femur, the guide bushing 16 is positioned at the lower lateral-most position of the notch guide 17 possible and the cutting element is advanced through the bone from the anterior side to the posterior side of the femur. The guide bushing 16 is then moved to the lower medial-most position of the notch face 17 and is again advanced through the femur.

An advantage of the system of the invention is that it provides a modular system that is useful to resect bone to accommodate prostheses of different sizes. Femoral notch guides are typically available in a variety of sizes such that the notch 50 is suitably sized to resect a bone to accommodate different types and sizes of prostheses. The guide system 10 of the invention can be affixed to different sized femoral notch guides. Thus, a standard sized face plate and guide bushing can be used to effect resection of the bone to accept different sized prostheses. One or more sets of cutting elements can be provided in a size and shape complementary to the desired guide bushing. The size of the intercondylar notch 104 that is cut in the bone can be controlled by varying the size of the femoral notch guide 17 with which the guide component 10 is used.

Alternatively, the system of the invention can include a variety of guide bushings that are removably and replaceably attachable to the guide component 10, each guide bushing being of a different, desired size.

The dimensions of the various components of the system of the invention can vary within ranges that will be appreciated by those having ordinary skill in the art. Further, one of ordinary skill in the art will readily appreciate that the system described above can be altered in terms of size, shape and application without departing from the scope of the invention. All references cited herein are expressly incorporated by reference in their entirety.

What is claimed is:

1. A surgical guide and cutting system, comprising:
    a first guide assembly mountable in proximity to a bone to be prepared, the guide assembly having a guide bushing that is removably and replaceably mountable thereon in alignment with a surface of a bone to be prepared; and at least one cutting element selectively insertable within the guide bushing, the cutting element having (i) a housing with a shape complementary to and able to fit within the guide bushing, and (ii) a rotatable bone cutting member disposed within the housing, the bone cutting member having a distal end with a bone cutting surface and a proximal end that protrudes from a proximal end of the housing.

2. The system of claim 1 wherein the first guide assembly is matable to a second guide component that is mounted upon the bone to be prepared.

3. A surgical guide and cutting system, comprising:

a first guide assembly mountable in proximity to a bone to be prepared, the guide assembly having a guide bushing that is removably and replaceably mountable on the first guide assembly in alignment with a surface of a bone to be prepared and being matable to a second guide component that is mounted upon the bone to be prepared;

at least one cutting element selectively insertable within the guide bushing, the cutting element having (i) a housing with a shape complementary to and able to fit within the guide bushing, and (ii) a rotatable bone cutting member disposed within the housing, the bone cutting member having a distal end with a bone cutting surface and a proximal end that protrudes from a proximal end of the housing;

a fixation block mountable upon the second guide component;

a face plate adjustably mounted upon the fixation block, the face plate having a bone-facing opening therein;

a locking element effective to secure the face plate in a desired position upon the fixation block; and means for affixing the guide bushing to the face plate such that the guide bushing communicates with the bone-facing opening.

4. The system of claim 2 wherein the second guide assembly is a femoral notch guide that is mountable upon a distal end of a femur to expose an anterior surface of the femur.

5. The system of claim 3 wherein the second guide assembly has at least one locking element and the first guide component has at least one lock engaging component on the fixation block effective to secure the first guide component to the second guide component.

6. The system of claim 1 wherein the at least one guide bushing has a substantially square or rectangular opening in alignment with the surface of the bone to be prepared.

7. The system of claim 6 wherein the substantially square opening of the guide bushing is in communication with the bone-facing opening of the face plate and has a size that is smaller than the bone-facing opening of the face plate.

8. The system of claim 7 wherein the guide bushing, when affixed to the face plate, is moveable both in a horizontal plane and a vertical plane.

9. The system of claim 6 wherein the system includes a plurality of guide bushings, each having a different size for the substantially square opening.

10. The system of claim 1 wherein the proximal end of the rotatable bone cutting element is attachable to a Hudson end power reamer effective to rotate the bone cutting element.

11. The system of claim 10 wherein the cutting element further includes a non-rotatable coupling means for linearly advancing the housing upon linear advancement of the rotatable bone cutting element.

12. The system of claim 3 wherein the means for affixing comprises:

a pair of opposed channels formed in the face plate;

a pair of opposed guide flanges formed on the guide bushing and matable within the opposed channels.

13. The system of claim 12 wherein the means for affixing further includes a locking mechanism effective to retain the opposed guide flanges within the opposed channels.

14. The system of claim 3 wherein the bone-facing opening in the face plate is rectangular.

15. The system of claim 1 wherein the proximal end of the rotatable bone cutting element includes a Hudson end.

16. The system of claim 13 wherein the opposed guide flanges of the guide bushing are matable within the opposed channels such that the guide bushing is able to move in the medial-lateral direction by approximately 0.05 to 0.30 inch and vertically by approximately 0.1 to 0.40 inch in either direction.

17. A surgical guide and cutting system, comprising:

a first guide assembly having a guide bushing with a square opening in communication with a bone to be prepared, the guide bushing being movable in both the horizontal and vertical directions by up to about 0.3 inch; and at least one cutting element selectively insertable within the guide bushing, the cutting element having (i) a housing with an external geometry and size sufficient to enable it to fit within the square opening of the guide bushing, and (ii) a rotatable bone cutting member disposed within the housing, the bone cutting member having a distal end with a bone cutting and chiseling surface features and a proximal connection end that protrudes from a proximal end of the housing.

* * * * *